(12) United States Patent
Begemann et al.

(10) Patent No.: US 6,629,931 B1
(45) Date of Patent: Oct. 7, 2003

(54) METHOD AND SYSTEM FOR MEASURING A SOURCE IMPEDANCE OF AT LEAST ONE CARDIAC ELECTRICAL SIGNAL IN A MAMMALIAN HEART

(75) Inventors: Malcolm J. Begemann, Velp (NL); Willem Boute, Dieren (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/705,806

(22) Filed: Nov. 6, 2000

(51) Int. Cl.$^7$ .................................... A61B 5/02
(52) U.S. Cl. ................... 600/508; 600/508; 600/547; 607/7; 607/8; 607/28
(58) Field of Search ............................ 600/547, 374, 600/504, 528; 607/7, 8, 9, 27, 28

(56) References Cited

U.S. PATENT DOCUMENTS

| | | | |
|---|---|---|---|
| 3,989,958 A | 11/1976 | Renirie et al. | |
| 3,989,959 A | 11/1976 | Renirie et al. | |
| 4,023,046 A | 5/1977 | Renirie | |
| 4,097,766 A | 6/1978 | Renirie | |
| 4,226,245 A * | 10/1980 | Bennett, Jr. | 128/419 PT |
| 4,275,737 A | 6/1981 | Thompson et al. | |
| 4,694,830 A | 9/1987 | Lekholm | |
| 4,702,253 A | 10/1987 | Nappholz et al. | |
| 4,884,576 A | 12/1989 | Alt | |
| 5,282,840 A | 2/1994 | Hudrlik | |
| 5,411,529 A * | 5/1995 | Hudrlik | 607/6 |
| 5,431,687 A | 7/1995 | Kroll | |
| 5,480,441 A | 1/1996 | Hudrlik | |
| 5,507,785 A | 4/1996 | Deno | |
| 5,562,711 A | 10/1996 | Yerich et al. | |
| 5,577,509 A | 11/1996 | Panescu et al. | |
| 5,603,725 A | 2/1997 | Schaldach | |
| 5,713,935 A | 2/1998 | Prutchi et al. | |
| 6,044,294 A * | 3/2000 | Mortazavi et al. | 600/547 |
| 6,141,585 A * | 10/2000 | Prutchi et al. | 607/8 |
| 6,269,264 B1 * | 7/2001 | Weyant et al. | 600/547 |

FOREIGN PATENT DOCUMENTS

WO  WO 92/02274  2/1992

OTHER PUBLICATIONS

PCT International Search Report, PCT/US 01/47663 (Aug. 16, 2002).

* cited by examiner

Primary Examiner—Hieu T. Vo
Assistant Examiner—Johnny H. Hoang

(57) ABSTRACT

A method of measuring a source impedance of at least one cardiac electrical signal in a mammalian heart is provided. A first amplifier system is operated. A first signal from a chamber of the heart is received. The first signal is passed through a first amplifier. A second amplifier system is then operated. A second signal from the chamber of the heart is received. The second signal is passed through a second amplifier. Finally, the source impedance of at least one cardiac electrical signal is calculated. The source impedance is based on the amplified first signal and the amplified second signal.

58 Claims, 8 Drawing Sheets

METHOD AND SYSTEM FOR MEASURING A SOURCE IMPEDANCE OF AT LEAST ONE CARDIAC ELECTRICAL SIGNAL IN A MAMMALIAN HEART

FIELD OF THE INVENTION

The present invention relates to cardiac pacing systems and methods, and, more particularly, to cardiac pacing systems, which provide for the measurement and processing of data related to the source impedance of electrical cardiac signals.

BACKGROUND OF THE INVENTION

In the introduction it should be clearly pointed out that all the prior art referred to related to the stimulus-impedance, i.e. the impedance that the tissue represents during the delivery of a (subthreshold) stimulus. Our invention relates to the source impedance of cardiac signals, either spontaneous ones or evoked ones.

Implanted cardiac pacemakers are employed to assist patients suffering from severe bradycardia or chronotropic incompetence. Originally, such pacemakers restored a normal, at rest, heart rate by providing either a fixed rate or a narrow range of externally programmable rates. However, these pacemakers failed to meet patients' metabolic demands during exercise. Consequently, so-called "rate adaptive" or "rate responsive" pacemakers were developed. These pacemakers sense one or more parameters correlated to physiologic need and adjust the pacing rate of the pacemaker accordingly.

One way to sense the above-stated parameter is to measure the impedance between a pacing electrodes. Various pulse-based impedance sensors have been proposed or are now in use with cardiac stimulators for deriving both hemodynamic and other physiologic parameters. Generally, these sensors deliver trains of fairly low-energy probing pulses between two or more electrodes of a pacing or defibrillation lead system. Each train contains pulses delivered at the rate of between 1 and 500 per second. In general, these pulses have a biphasic morphology in order to balance the charge delivered to the tissue, thus avoiding ion migration and electrolysis within the living tissue, as well as reducing interference on external monitoring equipment. In addition, charge balancing reduces the possibility of actually capturing the heart muscle by these low energy pulses with low-threshold leads.

However, the prior art has not developed an effective means by which to measure the source impedance of the cardiac electrical signals. In fact, the prior art referred to herein relates to the stimulus-impedance of the heart; i.e., the impedance that the tissue represents during the delivery of a (subthreshold) stimulus—not to the source impedance of cardiac signals, either spontaneous or evoked ones. For example, in Renirie et al., U.S. Pat. No. 3,989,958, there is provided an amplifier circuit for detecting low level signals of positive or negative amplitude, and for producing an output pulse whenever the input signal exceeds a predetermined threshold level. Although Renirie provides an example of an operational transconductance amplifier (OTA) sense amplifier, Renidie does not provide a means with which to sense the voltage (open source through a high input impedance amplifier) and the current (short-circuited source through low 'zero' input impedance amplifier) of the cardiac electrical signal.

Similarly, Renirie et al., U.S. Pat. No. 3,989,959, Renirie, U.S. Pat. No. 4,023,046, and Renirie, U.S. Pat. No. 4,097,766, all likewise provide examples of OTA (current-based) sense amplifiers.

In Thompson et al., U.S. Pat. No. 4,275,737, there is disclosed a cardiac pacemaker responsive to a natural heart activity for affecting the operation of the pacemaker. Thompson discloses an example of a high impedance sense amplifier. However, Thompson does not disclose the use of a current sensing amplifier.

Examples of minute volume-based rate responsive pacemakers utilizing a cardiac impedance measurement consisting of simultaneous current stimulus and voltage monitoring mechanisms are disclosed in Nappholz et al., U.S. Pat. No. 4,702,253, Aft, U.S. Pat. No. 4,884,576, and Yedch et al., U.S. Pat. No. 5,562,711. However, these patents measure the pacing impedance of the applied low-energy pulses and do not involve the simplified improvement of the present invention; that is, the measurement of a source impedance of cardiac signals based upon a voltage signal and a current signal.

In Hudrlik, U.S. Pat. No. 5,282,840, there is disclosed a physiological monitoring system for monitoring the condition of a patient's body tissue. Hudrlik discloses an impedance measurement system that uses a field density clamp for detecting ischemia as well as drug monitoring and titration.

In Kroll, U.S. Pat. No. 5,431,687, there is disclosed another implantable cardiac defibrillator. Kroll discloses another example of cardiac impedance sensing which senses the impedance of the heart during stimulus delivery.

Buldino, U.S. Pat. No. 5,507,785, and Prutchi et al., U.S. Pat. No. 5,713,935 disclose subthreshold biphasic current stimulus systems used to determine cardiac impedance during these stimuli. In Buldino and Prutchi, the cardiac impedance sensed is used for rate response; that is, for a minute volume and stroke volume, detection mechanisms.

Finally, in Panescu et al., U.S. Pat. No. 5,577,509, there is disclosed a method for examining heart tissue morphology using a pair of electrodes, at least one of which is located in contact with the heart tissue. Panescu examines the cardiac tissue through current-driven impedance measurements circuits. Additionally, Panescu uses multiplexing to facilitate data processing.

As discussed above, the most pertinent prior art patents are shown in the following table:

TABLE 1

Prior Art Patents.

| Patent No. | Date | Inventor(s) |
| --- | --- | --- |
| 3,989,958 | Nov. 02, 1976 | Renirie et al. |
| 3,989,959 | Nov. 02, 1976 | Renirie et al |
| 4,023,046 | May 10, 1977 | Renirie |
| 4,097,766 | Jun. 27, 1978 | Renirie |
| 4,275,737 | Jun. 30, 1981 | Thompson et al. |
| 4,702,253 | Oct. 27, 1987 | Nappholz et al. |
| 4,884,576 | Dec. 05, 1989 | Alt |
| 5,282,840 | Feb. 01, 1994 | Hudrlik |
| 5,431,687 | Jun. 11, 1995 | Kroll |
| 5,507,785 | Apr. 16, 1996 | Deno |
| 5,563,711 | Oct. 08, 1996 | Yerich et al. |
| 5,577,509 | Nov. 26, 1996 | Panescu et al. |
| 5,713,935 | Feb. 03, 1998 | Prutchi et al. |

All the patents listed in Table 1 are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a method and system for measuring and processing data related to the source impedance of at least one cardiac electrical signal in a mammalian heart. Such a system of the present invention adds important information to cardiac pacing systems related to the condition of the cardiac muscle and the electrical signals that it produces, currently not available in cardiac pacing systems.

The present invention has certain objects. That is, various embodiments of the present invention provide solutions to one or more problems existing in the prior art respecting the measurement of a source impedance of a cardiac electrical signal of a mammalian heart. Those problems include, without limitation: the ability to accurately measure both current and voltage with two different amplifier systems, the ability to switch between the two different amplifier systems and to process and store the data that was obtained for either immediate or later processing. Unlike the prior art above, the present invention relates to the stimulus-impedance (i.e., the impedance that the tissue represents during the delivery of a (subthreshold) stimulus), rather than the source impedance of spontaneous or evoked signals.

In comparison to known techniques for measuring cardiac parameters such as ischemia, the repolarization time period, various embodiments of the present invention may provide the following advantage, inter alia, i.e., the measurement of the source impedance of a cardiac electrical signal and switching between two differing amplifier systems.

Some of the embodiments of the present invention include one or more of the following features: an implantable medical device including at least one sensing lead, at least one pacing lead, a microprocessor and an input/output circuit including a digital controller/timer circuit, an output amplifier, a voltage sense amplifier, a current sense amplifier, a peak sense and threshold measurement device and a comparator. Furthermore, in accordance with the resent invention, a method of measuring a source impedance of at least one cardiac electrical signal in a mammalian heart is provided. A first amplifier system, e.g. the voltage sensing amplifier is operated. A first signal from a chamber of the heart is received. The first signal is passed through a first amplifier. A second amplifier system, e.g. the current sensing amplifier, is then operated. A second signal from the chamber of the heart is received. The second signal is passed through a second amplifier. Finally, the source impedance of the at least one cardiac electrical signal is calculated. The source impedance is based on the amplified first signal and the amplified second signal. The switching frequency between the two different amplifiers ranges from several kiloHerz, providing an accurate source impedance signal of every single electrical cardiac signal to once every beat, second up to minutes, providing a more averaged trend of the source impedance signal of the cardiac chamber.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
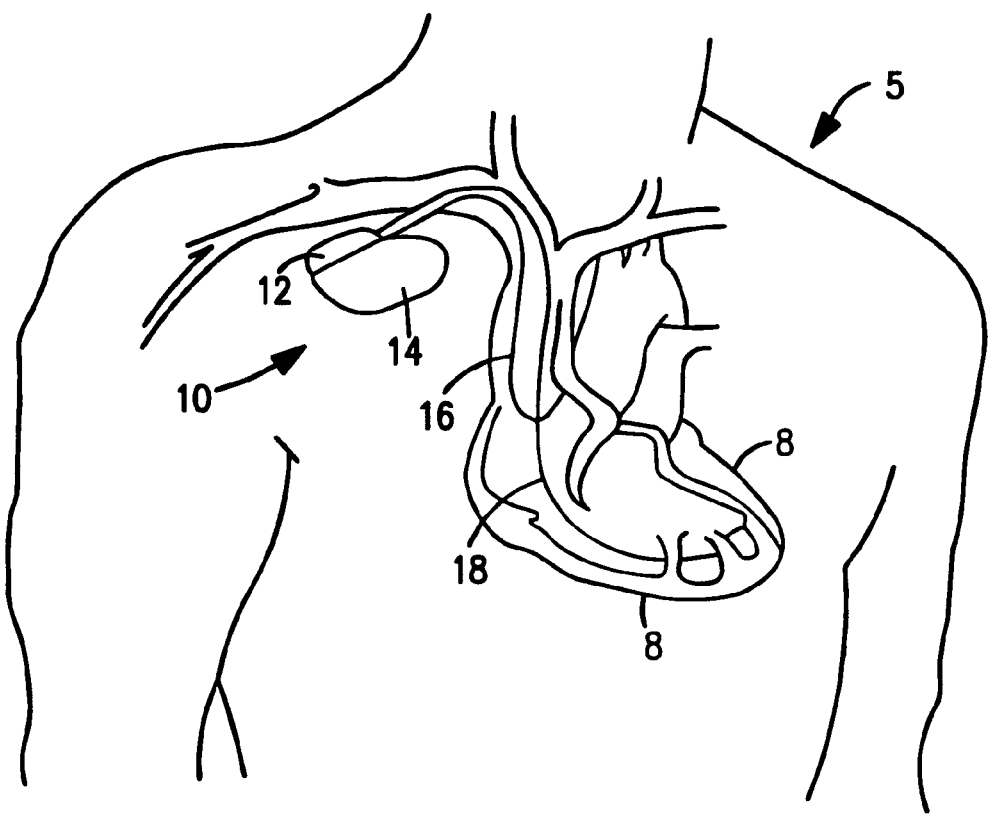
FIG. 1 is a schematic view of an embodiment of an implantable medical device, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 Shelton et al. or U.S. Pat. No. 5,144,949 Olson, all hereby incorporated by reference herein, each in its respective entirety.

Figure 2:
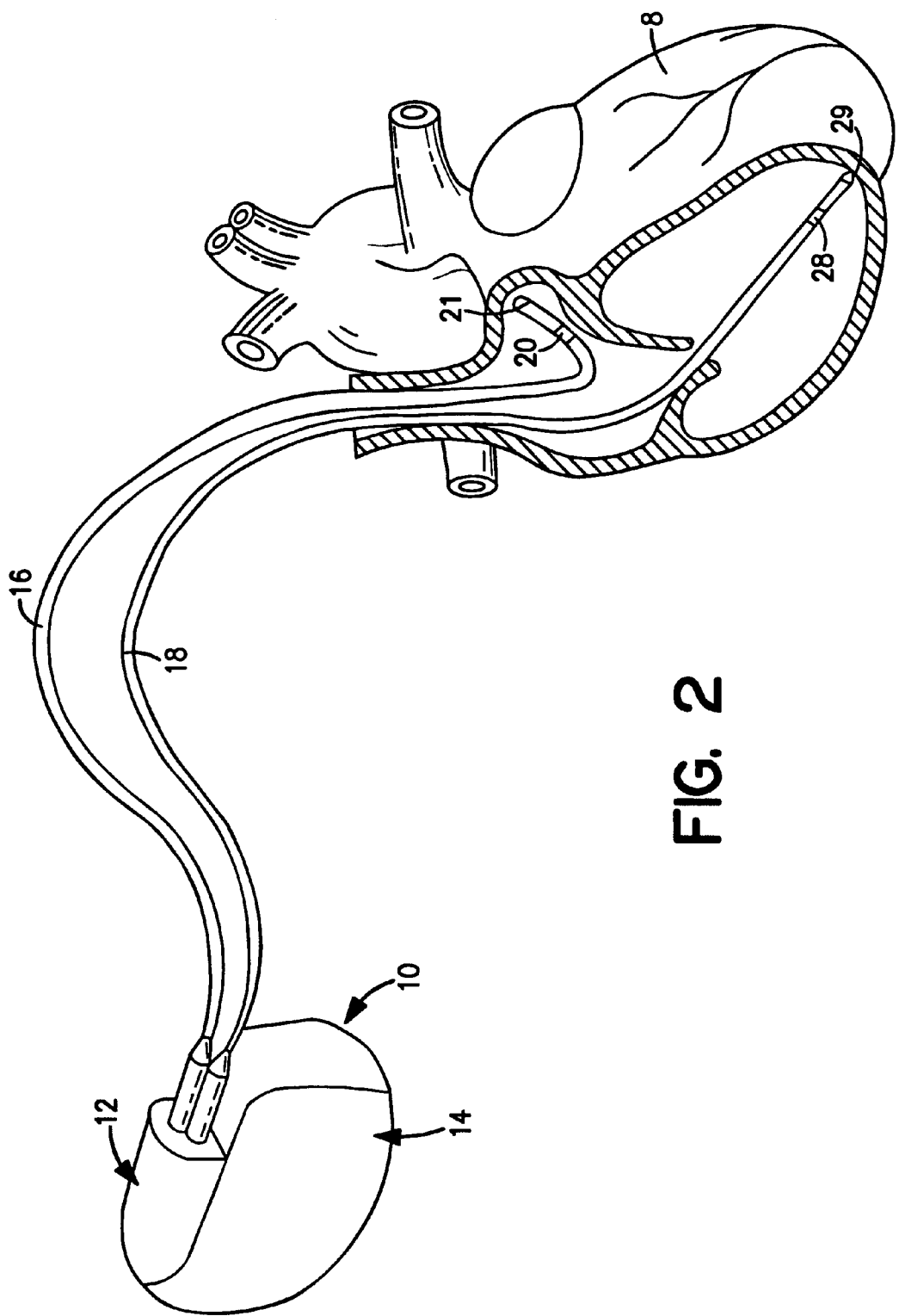
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
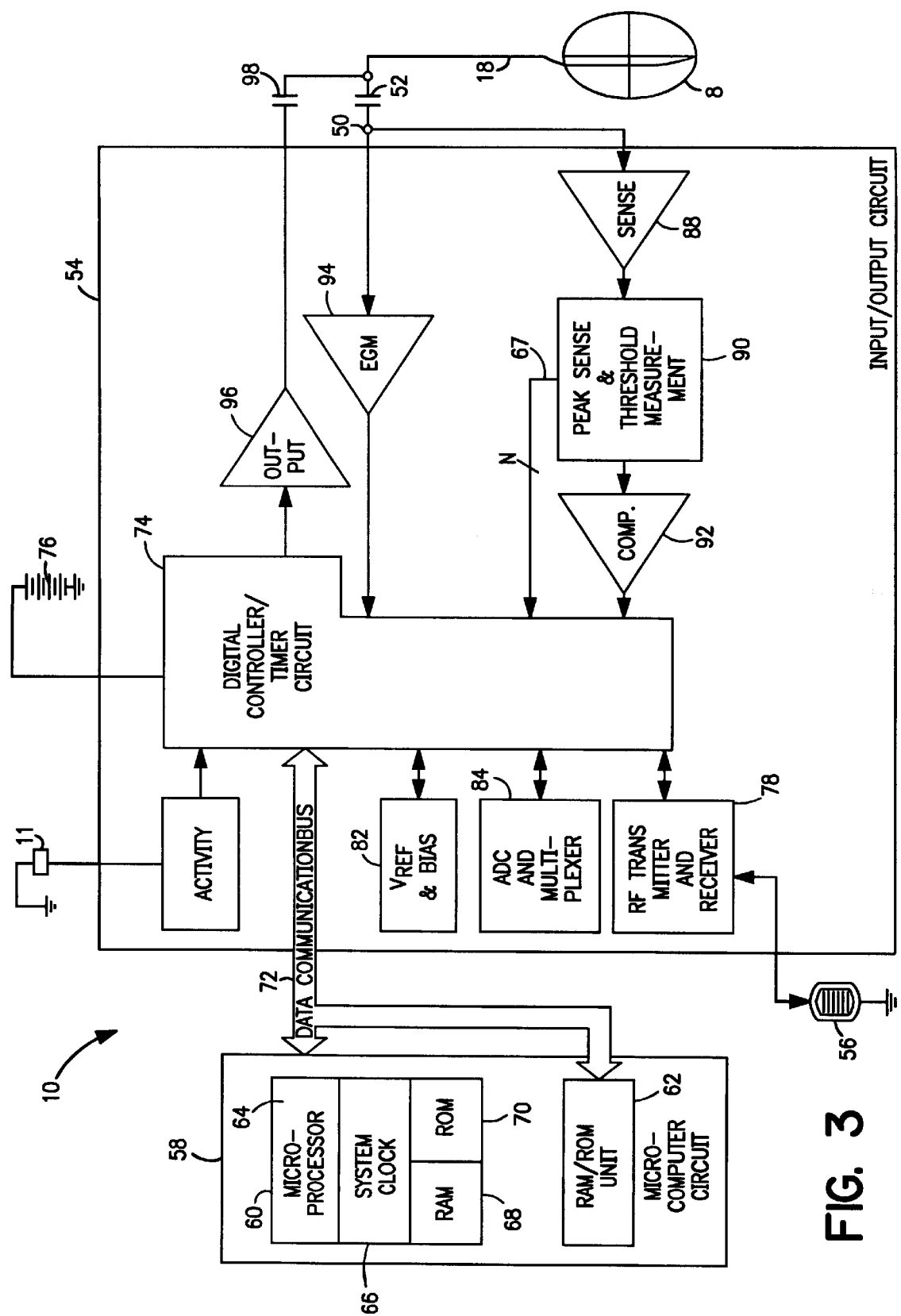
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued Thompson et al., hereby incorporated by reference herein in its entirety, or to that disclosed in the above-referenced '453 patent Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 Olson et al., U.S. Pat. No. 5,354,316 Keimel, U.S. Pat. No. 5,314,430 Bardy, U.S.

Pat. No. 5,131,388 Pless and U.S. Pat. No. 4,821,723 Baker et al., all hereby incorporated by reference herein, each in its respective entirety.

Figure 4:
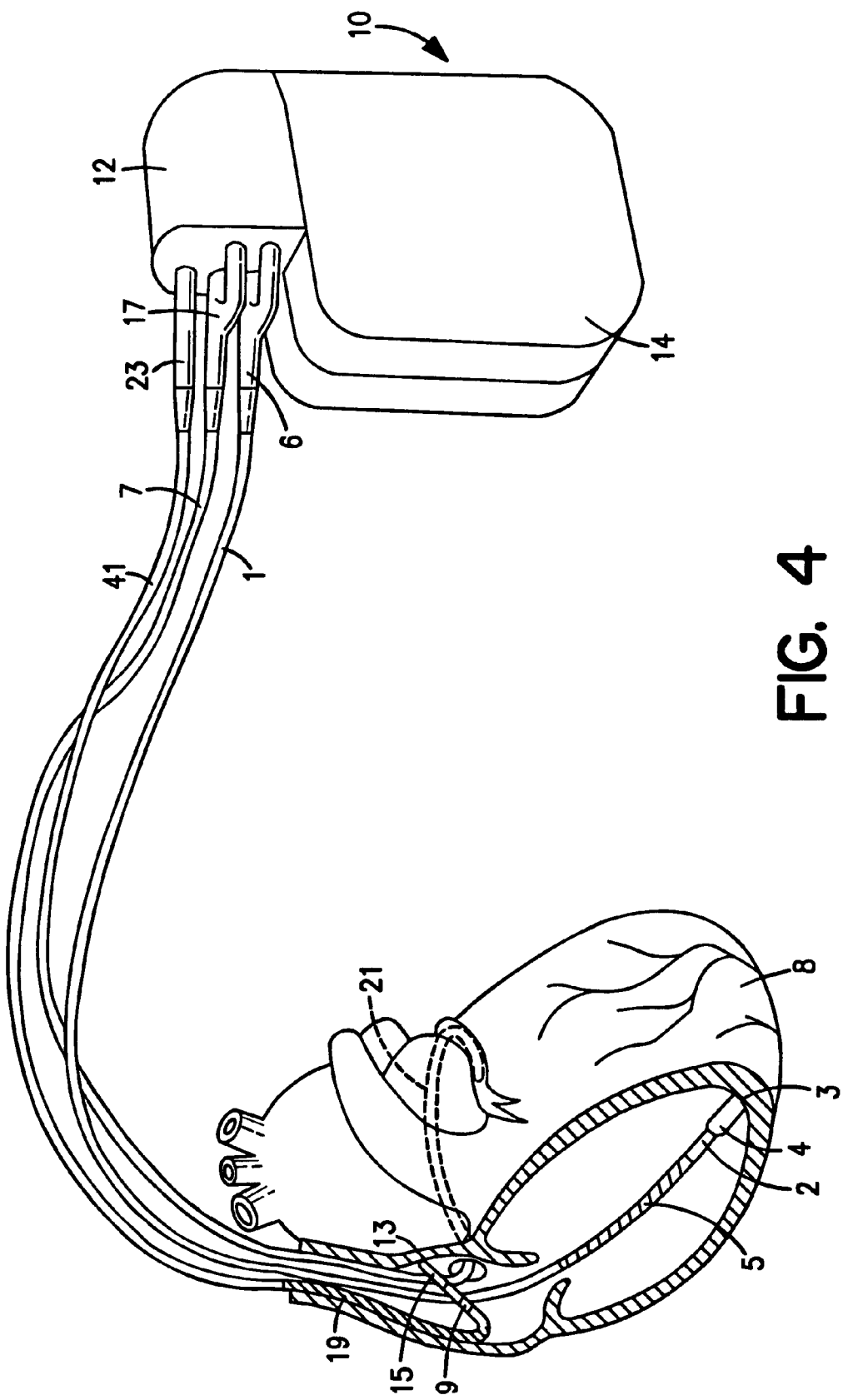
FIG. 4 illustrates another embodiment of an implantable medical device, made in accordance with the present invention.
Figure 5:
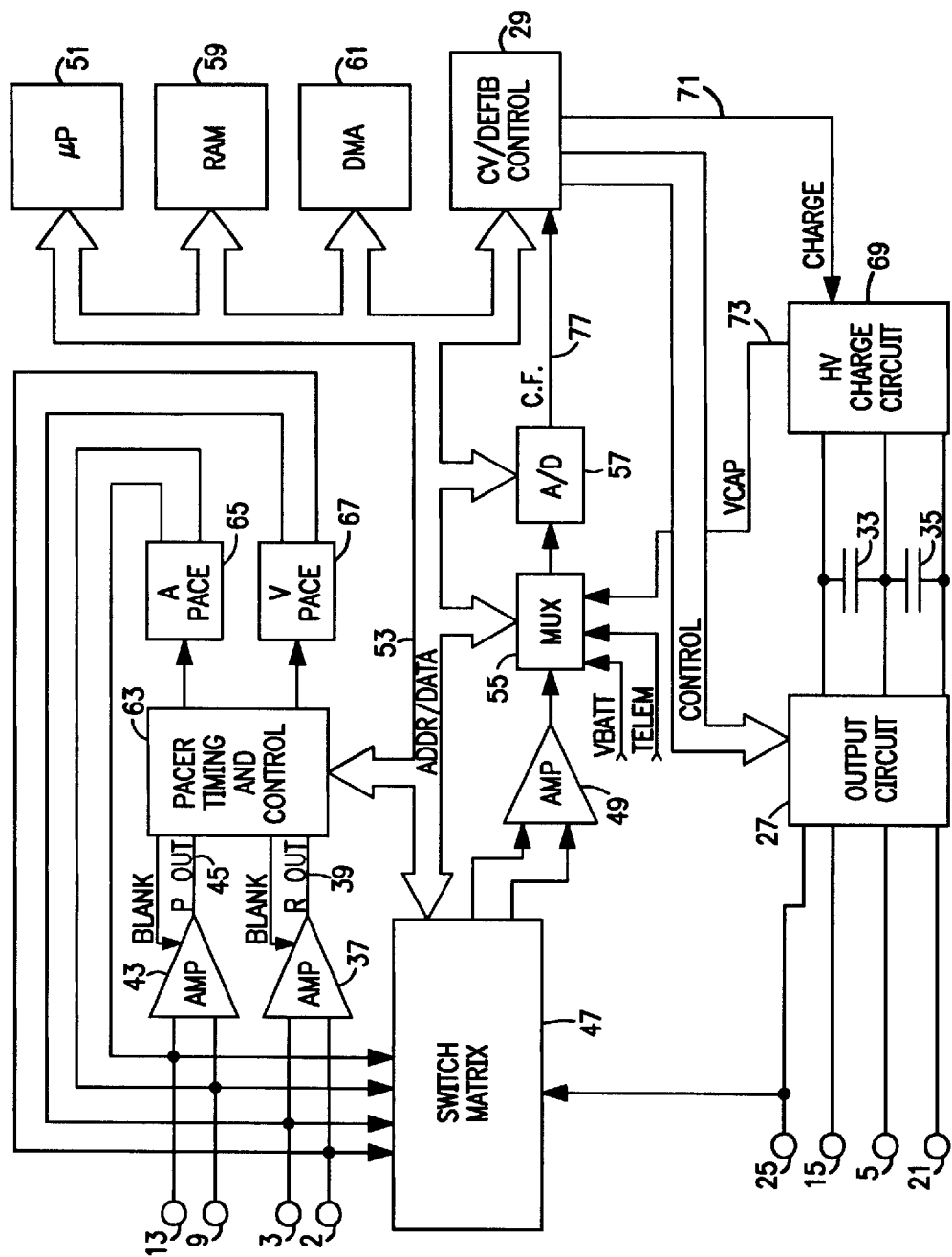
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor., The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier. 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT U.S. application Ser. No. 92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 Zipes, U.S. Pat. No. 4,949,719 Pless et al., or U.S. Pat. No. 4,375,817 Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 Keimel, also incorporated by reference herein in its entirety. Output control circuitry similar to that disclosed in U.S. Pat. No. 4,953,551 Mehra et al. or U.S. Pat. No. 4,800,883 Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 Obel et al., U.S. Pat. No. 5,207,218 Carpentier et al. or U.S. Pat. No. 5,330,507 Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Winstrom, which is incorporated by reference herein, in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 Obel et al., U.S. Pat. No. 5,207,218 Carpentier et al. or U.S. Pat. No. 5,330,507 Schwartz, or an implantable monitoring device such as that disclosed in U.S. Pat. No. 5,331,966 issued to Bennet et al., all of which are incorporated by reference herein, each in their respective entireties. The present invention is believed to find wide application to any form of implantable electrical device for use in conjunction with electrical leads.

The present invention comprises a means for measuring the source impedance of cardiac electrical signals by IMD 10 implanted in heart 8. Generally speaking, a method of measuring the source impedance of at least one cardiac electrical signal in a mammalian heart is provided. A first amplifier system is operated. A first signal from a chamber of the heart is received. The first signal is passed through a first amplifier. A second amplifier system is then operated. A second signal from the chamber of the heart is received. The second signal is passed through a second amplifier. Finally, the source impedance of the at least one cardiac electrical signal is calculated. The source impedance is based on the amplified first signal and the amplified second signal.

Figure 6:
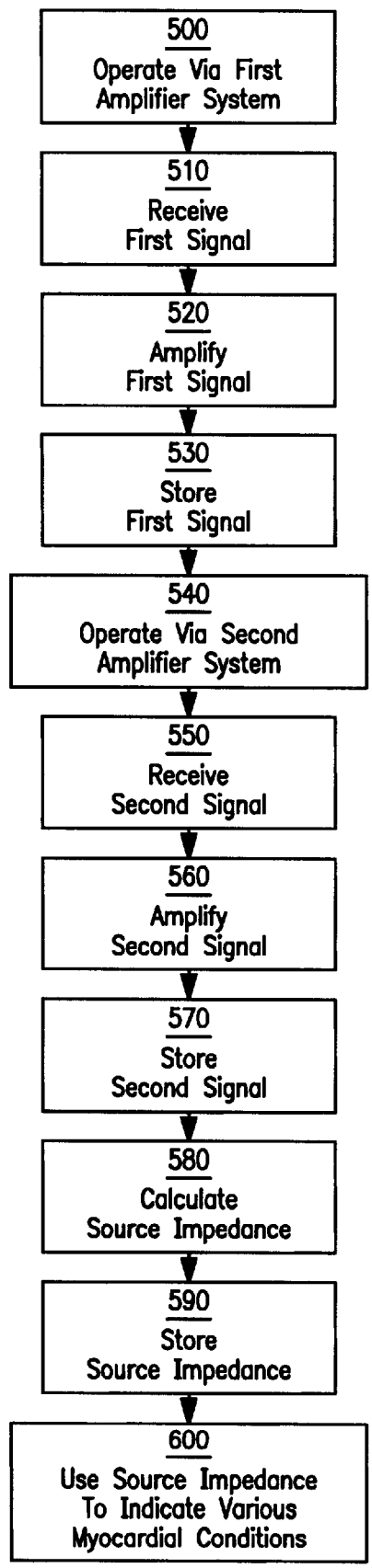
FIG. 6 illustrates a flow chart of a routine of one embodiment of a method for measuring the source impedance of at least one cardiac electrical signal from a mammalian heart, in accordance with the present invention.

FIG. 6 shows one embodiment of a method for measuring the source impedance of at least one cardiac electrical signal in a mammalian heart. The method for measuring the source impedance of the cardiac electrical signal may be preferably performed by means of a computer algorithm program and software, which may be stored integral with, or remote from, IMD 10. Alternatively, the method may be performed in any other similar manner.

The computer algorithm program may preferably by any program capable of being stored on an electronic medium, such as, for example, RAM 68 or ROM 70, and permitted to be accessed (and consequently run) by microprocessor 64. Alternatively, the method may be performed manually by a programmer, electronically programming instructions to IMD 10, either remotely from a location away from IMD 10, or via an electronic connection with IMD 10.

In Block 500, IMD 10 amplifies the signal(s) received from mammalian heart 8 via sensing leads 2, 3, 13, 19, using a first amplifier system. Sensing leads 2, 3, 13, 19, which are preferably low polarization leads, sense cardiac electrical signals received from mammalian heart 8. Preferably, the electrical signals obtained from sensing leads 2, 3, 13, 19 measure the depolarization and re-polarization of mammalian heart 8. In the embodiment illustrated in Block 500, the first amplifier system may be a high impedance sense amplifier system, similar to that described with respect to FIG. 7, below. The high impedance sense amplifier system used in the present invention is preferably used to measure the voltage of the cardiac electrical signals from mammalian heart 8.

Figure 7:
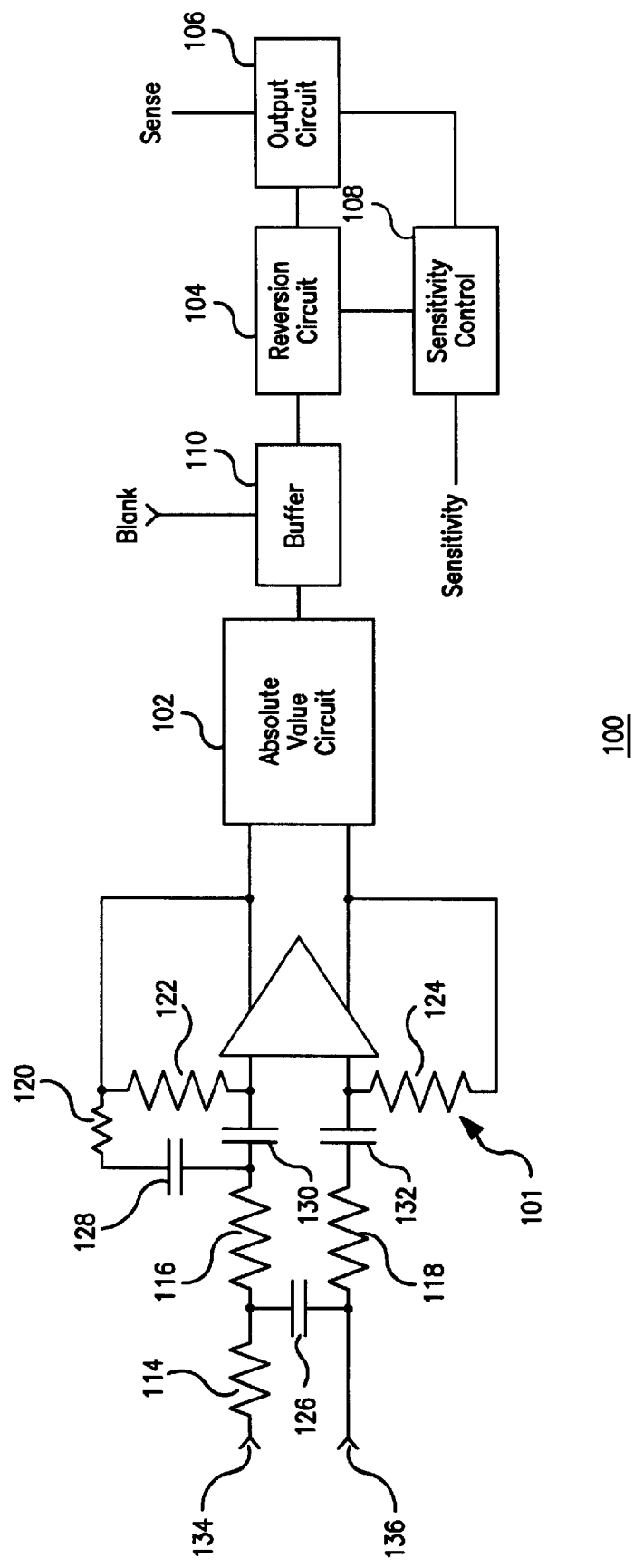
FIG. 7 illustrates one embodiment of a voltage amplifier, in accordance with the present invention.

FIG. 7 shows a block diagram of one embodiment of a sense amplifier circuit. The sense amplifier circuit, which is generally shown at 100, may include preamplifier section, indicated generally at 101, absolute value circuit 102, reversion circuit 104, output circuit 106 and sensitivity control circuit 108. Buffer 110 may be provided between absolute value circuit 102 and reversion circuit 104. Buffer 110 is preferably provided to prevent loading on absolute value circuit 102 from reversion circuit 104. Additionally, buffer 110 is responsive to the "BLANK" signal. The "BLANK" signal is used preferably to turn off and block signals from reversion circuit 104.

Preamplifier section 101 can be a differential input, differential output device having a dual feedback active filter. The dual feedback active filter can include resistors 114, 116, 118, 120, 122, 124 and capacitors 126, 128, 130, 132. Preamplifier section 101 can be designed to have an open loop gain of approximately 57,000 Hertz with a unity gain crossover point of approximately 2000 Hertz. The dual negative feedback method minimizes the number of external components used. The differential input of preamplifier section 101 allows an essentially polarity-independent degree of response to signals appearing at input terminals 134,136. That is, preamplifier section 101 can be essentially identically responsive to signals appearing at input terminals 134, 136, without regard to polarity. The differential output of preamplifier section 101 can provide two signals of opposite polarity (but of essentially the same absolute value), each being representative of signals appearing at input terminals 134, 136.

Absolute value circuit 102 can respond to the differential output signals of preamplifier section 101 to provide a single polarity signal representative of the signal sensed at input terminals 134, 136. Thus, preamplifier section 101 and absolute value circuit 102 may combine to provide signals of a single polarity representative of signals appearing at input terminals 134,136, but without regard to the polarity of the signals at input terminals 134, 136. In this way, the detecting circuitry contained within reversion circuit 104 need be responsive to signals only of a single polarity without creating a polarity disparity within sense amplifier circuit

100. The sensitivity of reversion circuit 104 to the output of absolute value circuit 102 can be controlled by sensitivity control circuit 108. The line between output circuit 106 and sensitivity control circuit 108 represents a known sensitivity hysteresis function.

Returning to FIG. 6, in Block 510, microprocessor 64 of IMD 10 receives a first signal from heart 8. The first signal may be received from heart 8 via any of the sensing circuitry and means described above, with regards to the sensing leads 2, 3,13,19. The first signal may be any cardiac electrical signal, such as, for example, a P-wave, a QRS wave, a T-wave, etc. Alternatively, the first signal may comprise an evocation of the cardiac signals described above; i.e., an evoked P-wave, an evoked QRS wave, an evoked T-wave, etc.

After receiving the first signal, computer algorithm software operating on microprocessor 64 of IMD 10 then sends an instruction to one the amplifiers 37, 43 to amplify the first signal. This step is illustrated in Block 520. The decision on which amplifier microprocessor 64 sends the instruction to amplify the first signal is dependent upon which amplifier is in use at that particular time. For example, if the signal received from heart 8 originates in the atrium, microprocessor instructs amplifier 43. Likewise, if the signal is from the ventricle, then amplifier 37 is utilized. Amplification of the first signal may occur through any of the means disclosed above with reference to FIGS. 3, 5 and/or 7.

Once the first signal is amplified, computer algorithm software operating on microprocessor 64 of IMD 10 stores the first signal in any of the memory locations disclosed above; specifically, on-board RAM 68 and ROM 70. This is provided for in Block 530.

In Block 540, computer algorithm software operating on microprocessor 64 of IMD 10 transmits an instruction signal, electronically switching IMD 10 so that IMD 10 operates via a second amplifier system. The second amplifier system amplifies the signal(s) received from mammalian heart 8 via sensing leads 2, 3,13, 19, which may, in one embodiment, preferably be low polarization leads. In the embodiment illustrated in Block 500, the second amplifier system may be a current sense amplifier system, similar to that described with respect to FIG. 8, below. The current sense amplifier system used in the present invention is preferably used to measure the signal current strength of the cardiac electrical signals from mammalian heart 8.

Preferably, the computer algorithm software operating on microprocessor 64 of IMD 10 may initiate the switch to the second amplifier system after a predetermined period of time. The predetermined period of time preferably ranges from a time relatively short in comparison to the duration of the cardiac signal (such as, for example, 0.1 msec, or any shorter amount) to one or more cardiac cycles. This allows microprocessor 64 of IMD 10 to record a number of samples of the source impedance during a single cardiac event. This provides many source impedance samples during a single cardiac event, and, in fact, produces a source impedance picture of that same cardiac event. Additionally, the predetermined period of time allows microprocessor 64 of IMD 10 to perform a great variety of myocardial actions (described below), as well as to maintain long-term information of the source impedance of heart 8. When one, more or several cardiac cycles are used as the period of time, such a time interval also allows microprocessor 64 to produce a source impedance that reflects a certain period of time.

Figure 8:
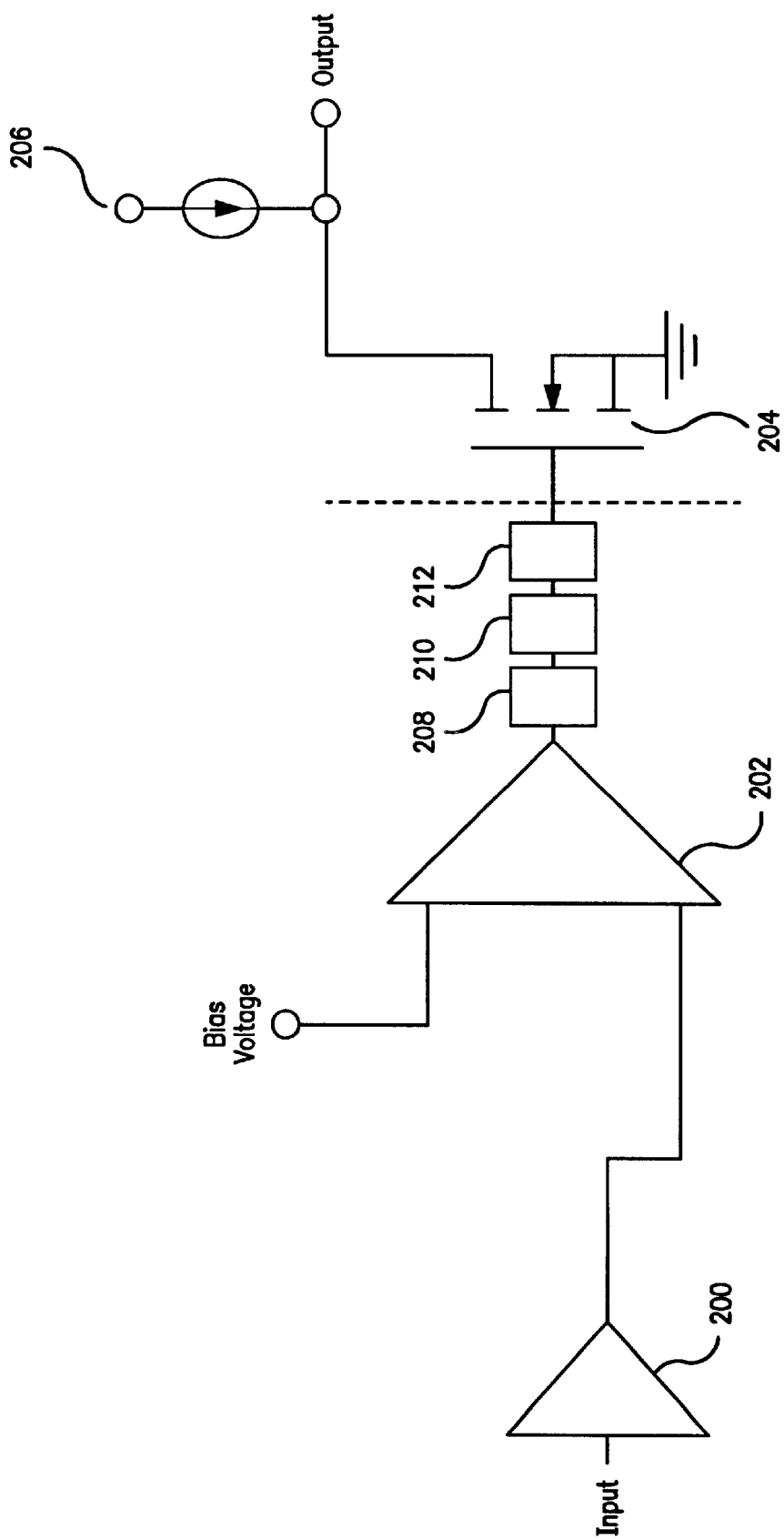
FIG. 8 illustrates one embodiment of a current amplifier, in accordance with the present invention.

FIG. 8 shows one embodiment of a configuration around which the various embodiments of the current sensing system of the present invention can be constructed. As shown, there is a first current sensing system 200. The first current sensing system 200 can operate as a known amplifier stage. The current sensing system 200 may preferably be any voltage amplifier system currently known in the art. Furthermore, the current sensing system 200 may include circuits relating to filtering 208, reversion 210 and level detection 212. Additionally, amplifier 200 can act as a current sensing amplifier with 'zero' input impedance. In such a case, amplifier 200 provides an output which can be proportional to the differential input current placed across the two input terminals of amplifier 200. The polarity of the output signal can be dependent upon the polarity of the differential input current. Amplifier 200 can have a special bias current terminal for receiving bias current. The bias current terminal can determine the essential characteristics of the current sensing amplifier 200. These characteristics may include the transconductance and the current drain. As used in the present invention, the output of first stage amplifier 200 can be directly connected to second stage amplifier 202, which is utilized as a comparator device. Of the two input terminals of second stage amplifier 202, one receives the output of the first stage amplifier, in either an inverting or non-inverting mode, and the other receives a bias voltage. The quiescent voltage difference across the two terminals can establish the magnitude of input swing required to cause a change in polarity of the output signal from second stage amplifier 202. Thus, if the amplitude of the signal coming from current sensing amplifier is larger than a fixed reference level established across the differential inputs of second stage amplifier 202, and opposite in polarity, the input voltage of second stage amplifier 202 changes from one polarity to another, thus switching second stage amplifier 202 output signal. In practice, the voltage gain of the amplifier stage is generally between 10 Volts and 20 Volts. The voltage gain may be one of the determinants of the swing in the input level to the first amplifier stage to switch the output of second stage amplifier 202.

Still referring to FIG. 8, the output of second stage amplifier 202 can be coupled into the gate of the CMOS transistor 204, which as shown has its source connected to ground and its drain connected to a current source 206. Because second stage amplifier 202 is a current source itself, and the input resistance of a CMOS transistor is extremely high, the voltage gain of second stage amplifier 202 is very high. For example, for a transconductance of 2 $\mu$A and an internal resistance of 75–109 Ohms, the gain is 150,000 Volts. This extremely high gain provides a very high switching response. Thus, as soon as the input to first stage amplifier 200 exceeds a predetermined signal threshold, the output of second stage amplifier 202 switches essentially instantly from a negative to a positive current, thus driving transistor 204 conductive and producing a voltage change at the output terminal suitable for driving the output load connected thereto.

Returning to FIG. 6, in Block 550, IMD 10 receives a second signal from heart 8. The second signal may be received from heart 8 via any of the sensing means described above. Similar to the first signal, the second signal may be any cardiac electrical signal, such as, for example, a P-wave, a ORS wave, a T wave, etc. Additionally, the second signal may comprise an evocation of the cardiac signals, also as described above. Furthermore, the second signal may be the same signal as the first signal.

After receiving the second signal, computer algorithm software operating on microprocessor 64 of IMD 10 then sends an instruction to one the amplifiers 37, 43 to amplify the second signal. This step is provided for in Block 560. The decision on which amplifier microprocessor 64 sends the instruction to amplify the second signal is dependent upon which amplifier is in use at the particular time. For example, if the signal received from heart 8 originates in the atrium, microprocessor instructs amplifier 43; if the signal is from the ventricle, then amplifier 37 is utilized. Amplification of the second signal may occur through any of the means disclosed above with reference to FIGS. 3, 5 and/or 7.

Once the second signal is amplified, computer algorithm software located on microprocessor 64 of IMD 10 stores the second signal in any of the memory locations disclosed above; specifically, on-board RAM 68 and ROM 70. This is provided for in Block 570.

In Block 580, computer algorithm software located on microprocessor 64 of IMD 10 then calculates the source impedance of the calculated cardiac electrical signal. In one embodiment, this is accomplished by dividing the voltage calculated from the first signal by the current calculated from the second signal. Alternatively, the source impedance may be calculated in any other known manner.

Once the source impedance is calculated, computer algorithm software located on microprocessor 64 of IMD 10 stores the source impedance in any of the memory locations disclosed above; preferably, on-board RAM 68 and ROM 70. This is provided for in Block 590.

Finally, as is illustrated by Block 600, the source impedance may be used to indicate a variety of myocardial conditions. For example, patients with an impaired cardiac function, such as, for example, heart failure, may require a different pacemaker therapy during exercise and recovery, such as, for example, rate responsive parameters, multi-site pacing, etc. Secondly, patients with angina pectoris may also require a different pacemaker therapy, such as, for example, a lower maximum heart rate. Finally, knowing the status of the myocardium at the site of the electrode may reveal systolic and diastolic interval information, which is useful in a variety of pacing modes. Alternatively, the source impedance may be further processed by the microprocessor 64. Examples of further processing of microprocessor 64 include long-term trending and beat-to-beat comparisons by microprocessor 64, etc.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for measuring the source impedance of a mammalian heart. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method of measuring a source impedance of at least one cardiac electrical signal in a mammalian heart, comprising:

operating a first amplifier system that is a voltage amplifier or a current sensing amplifier;
   receiving a first signal from a chamber of the heart;
   passing the first signal through a first amplifier;
   switching to a second amplifier system that is the voltage amplifier or the current sensing amplifier;
   receiving a second signal from the chamber of the heart;
   passing the second signal through a second amplifier; and
   calculating the source impedance of the at least one cardiac electrical signal based on the amplified first signal and the amplified second signal.

2. The method of claim 1, further comprising using the source impedance to indicate a variety of myocardial conditions.

3. The method of claim 1, further comprising storing the first signal prior to switching to the second amplifier system.

4. The method of claim 1, further comprising storing the second signal prior to calculating the source impedance.

5. The method of claim 1, further comprising storing the source impedance.

6. The method of claim 1, further comprising switching to the second amplifier system after a predetermined period of time.

7. The method of claim 6, wherein the predetermined period of time equals one cardiac cycle of the heart.

8. The method of claim 6, wherein the predetermined period of time equals 0.1 ms.

9. The method of claim 1, wherein the voltage amplifier measures a voltage of the first signal.

10. The method of claim 1, wherein the current sensing amplifier measures a current strength of the second signal.

11. The method of claim 1, wherein the chamber is a ventricle of the heart.

12. The method of claim 1, wherein the chamber is an atrium of the heart.

13. The method of claim 1, wherein the at least one cardiac electrical signal comprises a P-wave.

14. The method of claim 1, wherein the at least one cardiac electrical signal comprises a QRS wave.

15. The method of claim 1, wherein the at least one cardiac electrical signal comprises a T-wave.

16. The method of claim 1, wherein the second signal and the first signal comprise the same signal.

17. An implantable medical device comprising:

a processor;
   a controller operably connected to the processor; and
   at least one sense amplifier operably connected to the controller; wherein
   a source impedance is calculate by the processor based on a first signal received by the controller and amplified by one of the at least one sense amplifiers that is a voltage amplifier or a current sensing amplifier and a second signal received by the controller and amplified by one of the at least one sense amplifier that is the voltage amplifier or the current sensing amplifier.

18. The implantable medical device of claim 17, further comprising using the calculated source impedance to indicate a variety of myocardial conditions.

19. The implantable medical device of claim 17, further comprising storing the first signal prior to receiving the second signal.

20. The implantable medical device of claim 17, further comprising storing the second signal prior to calculating the source impedance.

21. The implantable medical device of claim 17, further comprising storing the source impedance.

22. The implantable medical device of claim 17, further comprising receiving the second signal after a predetermined period of time.

23. The implantable medical device of claim 22, wherein the predetermined period of time equals one cardiac cycle of the heart.

24. The implantable medical device of claim 22, wherein the predetermined period of time equals 0.1 ms.

25. The implantable medical device of claim 17, wherein the voltage amplifier measures a voltage of the first signal.

26. The implantable medical device of claim 17, wherein the chamber is a ventricle of the heart.

27. The implantable medical device of claim 17, wherein the chamber is an atrium of the heart.

28. The implantable medical device of claim 17, wherein the second signal and the first signal comprise the same signal.

29. A implantable medical device system for measuring a source impedance of at least one cardiac electrical signal in a mammalian heart, comprising:

means for operating a first amplifier system that is a voltage amplifier or a current sensing amplifier;

means for receiving a first signal from a chamber of the heart;

means for passing the first signal through a first amplifier;

means for switching to a second amplifier system that is the voltage amplifier or the current sensing amplifier;

means for receiving a second signal from the chamber of the heart;

means for passing the second signal through a second amplifier; and means for calculating the source impedance of the at least one cardiac electrical signal based on the amplified first signal and the amplified second signal.

30. The implantable medical device system of claim 29, further comprising means for using the source impedance to indicate a variety of myocardial conditions.

31. The implantable medical device system of claim 29, further comprising means for storing the first signal prior to switching to the second amplifier system.

32. The implantable medical device system of claim 29, further comprising means for storing the second signal prior to calculating the source impedance.

33. The implantable medical device system of claim 29, further comprising means for storing the source impedance.

34. The implantable medical device system of claim 29, further comprising means for switching to the second amplifier system after a predetermined period of time.

35. The implantable medical device system of claim 34, wherein the predetermined period of time equals one cardiac cycle of the heart.

36. The implantable medical device system of claim 34, wherein the predetermined period of time equals 0.1 ms.

37. The implantable medical device system of claim 29, wherein the voltage amplifier measures a voltage of the first signal.

38. The implantable medical device system of claim 29, wherein the chamber is a ventricle of the heart.

39. The implantable medical device system of claim 29, wherein the chamber is an atrium of the heart.

40. The implantable medical device system of claim 29, wherein the at least one cardiac electrical signal comprises a P-wave.

41. The implantable medical device system of claim 29, wherein the at least one cardiac electrical signal comprises a QRS wave.

42. The implantable medical device system of claim 29, wherein the at least one cardiac electrical signal comprises a T-wave.

43. The implantable medical device system of claim 29, wherein the second signal and the first signal comprise the same signal.

44. A computer usable medium for storing a program for measuring a source impedance of at least one cardiac electrical signal in a mammalian heart, comprising:

computer readable program code that operates a first amplifier system that is a voltage amplifier or a current sensing amplifier;

computer readable program code that receives a first signal from a chamber of the heart;

computer readable program code that passes the first signal through a first amplifier;

computer readable program code that switches to a second amplifier system that is the voltage amplifier or the current sensing amplifier;

computer readable program code that receives a second signal from the chamber of the heart;

computer readable program code that passes the second signal through a second amplifier; and computer readable program code that calculates the source impedance of the at least one cardiac electrical signal based on the amplified first signal and the amplified second signal.

45. The program of claim 44, further comprising:computer readable program code that uses the source impedance to indicate a variety of myocardial conditions.

46. The program of claim 44, further comprising computer readable program code that stores the first signal prior to switching to the second amplifier system.

47. The program of claim 44, further comprising computer readable program code that stores the second signal prior to calculating the source impedance.

48. The program of claim 44, further comprising computer readable program code that stores the source impedance.

49. The program of claim 44, further comprising computer readable program code that switches to the second amplifier system after a predetermined period of time.

50. The program of claim 49, wherein the predetermined period of time equals one cardiac cycle of the heart.

51. The program of claim 49, wherein the predetermined period of time equals 0.1 ms.

52. The program of claim 44, wherein the voltage amplifier measures a voltage of the first signal.

53. The program of claim 44, wherein the chamber is a ventricle of the heart.

54. The program of claim 44, wherein the chamber is an atrium of the heart.

55. The program of claim 44, wherein the at least one cardiac electrical signal comprises a P-wave.

56. The program of claim 44, wherein the at least one cardiac electrical signal comprises a QRS wave.

57. The program of claim 44, wherein the at least one cardiac electrical signal comprises a T-wave.

58. The program of claim 44, wherein the second signal and the first signal comprise the same signal.

* * * * *